(12) United States Patent
Ren et al.

(10) Patent No.: US 10,517,712 B2
(45) Date of Patent: Dec. 31, 2019

(54) BIFURCATED MEDICAL DEVICE FOR TREATING A TARGET SITE AND ASSOCIATED METHOD

(71) Applicant: St. Jude Medical, Cardiology Division, Inc., St. Paul, MN (US)

(72) Inventors: Brooke Ren, Maple Grove, MN (US); Daniel O. Adams, Long Lake, MN (US); John C. Oslund, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 652 days.

(21) Appl. No.: 15/255,233

(22) Filed: Sep. 2, 2016

(65) Prior Publication Data

US 2016/0367355 A1    Dec. 22, 2016

Related U.S. Application Data (63) Continuation of application No. 12/205,083, filed on Sep. 5, 2008, now abandoned.

(51) Int. Cl.
*A61F 2/07* (2013.01)
*B21F 45/00* (2006.01)
(Continued)

(52) U.S. Cl.
CPC ............... *A61F 2/07* (2013.01); *A61F 2/90* (2013.01); *B21F 45/008* (2013.01); *A61F 2/848* (2013.01);
(Continued)

(58) Field of Classification Search
CPC ...... B21F 27/02; B21F 27/021; B21F 45/008; A61F 2/07; A61F 2/82; A61F 2/86; A61F 2/90; A61F 2220/0091; A61F 2240/001
See application file for complete search history.

(56) References Cited

U.S. PATENT DOCUMENTS

| | | | |
|---|---|---|---|
| 4,655,771 A | 4/1987 | Wallsten et al. | |
| 5,398,586 A * | 3/1995 | Akiyama | D04C 1/06 87/6 |

(Continued)

FOREIGN PATENT DOCUMENTS

| | | |
|---|---|---|
| EP | 0734235 B1 | 2/1992 |
| WO | 95/16406 A1 | 6/1995 |

*Primary Examiner* — Edward T Tolan
(74) *Attorney, Agent, or Firm* — Armstrong Teasdale LLP (57) ABSTRACT

Embodiments of the present invention provide medical devices and methods for treating a target site within the body. For example, one embodiment provides a stent graft for treating a target site proximate to a bifurcated lumen, wherein the stent graft includes a first tubular structure having proximal and distal ends and a side wall extending therebetween. The first tubular structure includes an opening defined within the side wall and is configured to define a first portion having first and second ends and a second portion having first and second ends. The opening corresponds to the first ends of the first and second portions and the second ends of the first and second portions respectively correspond to the proximal and distal ends of the first tubular structure, and at least a portion of the first and second portions are configured to be positioned within respective branches of a bifurcated lumen.

18 Claims, 9 Drawing Sheets

(51) Int. Cl.
*A61F 2/90* (2013.01)
*A61F 2/06* (2013.01)
*A61F 2/848* (2013.01)

(52) U.S. Cl.
CPC . *A61F 2002/067* (2013.01); *A61F 2210/0076* (2013.01); *A61F 2220/0091* (2013.01); *A61F 2230/0034* (2013.01); *A61F 2240/001* (2013.01); *A61F 2250/0039* (2013.01); *A61F 2250/0067* (2013.01); *A61F 2250/0098* (2013.01)

(56) References Cited

U.S. PATENT DOCUMENTS

| | | |
|---|---|---|
| 5,507,769 A | 4/1996 | Marin et al. |
| 5,575,817 A | 11/1996 | Martin |
| 5,904,713 A | 5/1999 | Leschinsky |
| 6,027,516 A | 2/2000 | Kolobow et al. |
| 6,051,020 A * | 4/2000 | Goicoechea ............. A61F 2/82 623/1.35 |
| 6,129,756 A | 10/2000 | Kugler et al. |
| 6,200,339 B1 | 3/2001 | Leschinsky et al. |
| 6,287,335 B1 | 9/2001 | Drasler et al. |
| 6,325,822 B1 | 12/2001 | Chouinard et al. |
| 6,409,750 B1 | 6/2002 | Hyodoh et al. |
| 6,454,796 B1 * | 9/2002 | Barkman ............... A61F 2/07 623/1.35 |
| 6,626,939 B1 | 9/2003 | Burnside et al. |
| 6,663,665 B2 | 12/2003 | Shaolian et al. |
| 6,682,557 B1 | 1/2004 | Quiachon et al. |
| 6,773,453 B2 | 8/2004 | Ravenscroft |
| 6,802,859 B1 | 10/2004 | Pazienza et al. |
| 6,932,837 B2 | 8/2005 | Amplatz et al. |
| 6,956,475 B1 | 10/2005 | Hill |
| 7,004,967 B2 | 2/2006 | Chouinard et al. |
| 7,122,052 B2 | 10/2006 | Greenhalgh et al. |
| 8,414,635 B2 * | 4/2013 | Hyodoh ............... A61F 2/90 623/1.11 |
| 2002/0042644 A1 | 4/2002 | Greenhalgh |
| 2002/0111674 A1 | 8/2002 | Chouinard et al. |
| 2002/0156521 A1 * | 10/2002 | Ryan ................ A61F 2/07 623/1.13 |
| 2003/0023299 A1 * | 1/2003 | Amplatz ............ A61F 2/856 623/1.13 |
| 2003/0040771 A1 * | 2/2003 | Hyodoh ............. A61F 2/90 606/200 |
| 2004/0215332 A1 | 10/2004 | Frid |
| 2005/0010281 A1 | 1/2005 | Yodfat et al. |
| 2005/0033416 A1 | 2/2005 | Seguin et al. |
| 2005/0049676 A1 | 3/2005 | Nazzaro et al. |
| 2005/0131516 A1 | 6/2005 | Greenhalgh et al. |
| 2005/0234542 A1 | 10/2005 | Melsheimer et al. |
| 2006/0025851 A1 | 2/2006 | Khan et al. |
| 2006/0161244 A1 | 7/2006 | Seguin |
| 2007/0118207 A1 | 5/2007 | Amplatz et al. |
| 2007/0156229 A1 | 7/2007 | Park |
| 2008/0103587 A1 | 5/2008 | Henderson et al. |
| 2008/0221600 A1 * | 9/2008 | Dieck ............ A61B 17/12022 606/157 |
| 2009/0005847 A1 | 1/2009 | Adams |
| 2010/0030321 A1 * | 2/2010 | Mach ................ A61F 2/07 623/1.18 |
| 2010/0137969 A1 * | 6/2010 | Rakos ............... A61F 2/06 623/1.13 |

* cited by examiner

BIFURCATED MEDICAL DEVICE FOR TREATING A TARGET SITE AND ASSOCIATED METHOD

CROSS-REFERENCE TO RELATED APPLICATIONS

This application is a continuation application of U.S. patent application Ser. No. 12/205,083, filed on Sep. 5, 2008, the entire contents and disclosure of which are hereby incorporated herein by reference in their entirety.

BACKGROUND OF THE INVENTION

1) Field of the Invention

The present invention relates to medical devices and, in particular, to a medical device for treating a target site within the body, such as a vascular abnormality, proximate to a bifurcated lumen.

2) Description of Related Art

An aortic aneurysm is a weak area in the aorta, the main blood vessel that carries blood from the heart to the rest of the body. A common aneurysm is the abdominal aortic aneurysm ("AAA"), which may be caused by arteriosclerosis. As blood flows through the aorta, the weak vessel wall thins over time and expands like a balloon and can eventually burst if the vessel wall gets too thin. Most commonly, aortic aneurysms occur in the portion of the vessel below the renal artery origins. The aneurysm may be located in the vessels supplying the hips and pelvis, including the iliac arteries.

Rather than performing surgery to repair an aneurysm, vascular surgeons may install an endovascular stent graft delivered to the site of the aneurysm using elongated catheters. A stent graft can be used for a variety of conditions involving the blood vessels, but most commonly is used to reinforce an aneurysm. The stent graft may be delivered to a location bridging the aneurysm, at which point the stent graft is deployed and expanded to approximately the normal diameter of the aorta at that location. Over time, the stent graft becomes endothelialized and the space between the outer wall of the stent graft and the aneurysm ultimately fills with clotted blood, which prevents the aneurysm from growing further since the stent graft bypasses (excludes) the aneurysm and prohibits systematic pressure and flow on the weakened segment of the lumen.

Depending on where the aneurysm is in relation to other branch vessels, different design variations may be needed. For example, in treating an AAA, the stent graft should be placed so as not to exclude blood flow through the renal arteries which branch off from the abdominal aorta. Moreover, the stent graft should be anchored within the lumen to reduce the incidence of migration, such as by promoting endothelialization or fixation with the lumen. Endoleaks may occur as a result of blood flowing around the stent, which may result in further weakening of the site of the aneurysm.

In order to treat an AAA, bifurcated stent grafts have been employed. In particular, the bifurcated stent graft typically includes a main portion configured to bridge the aneurysm below the renal arteries and a pair of tubular portions extending from the main portion that are configured to extend into respective iliac arteries. The bifurcated stent graft is most commonly delivered through one of the iliac arteries. Thus, the delivery of the bifurcated stent graft may be complicated when attempting to position the tubular portions of the bifurcated stent graft into respective iliac arteries while also ensuring that the main portion is secured within the aorta upstream of the aneurysm without blocking the renal arteries.

Furthermore, the size of the delivery catheter may affect the ability of the surgeon to manipulate the catheter within the lumen, often reduced in size due to arteriosclerosis, and may result in trauma to the vascular tissue. Thus, the smaller the delivery catheter, the less trauma to the tissue should occur, and the medical device should be more easily and accurately positioned within the lumen. Smaller delivery catheters would also allow a physician access to smaller vessels, so as to more proactively treat aneurysms. Also, smaller aneurysms are typically easier to treat than larger aneurysms (e.g., aneurysms of at least 5 cm in diameter) because smaller aneurysms are more centrally located between the renal arteries and the iliac bifurcation and also because small aneurysms are more symmetrical and usually do not yet include tortuosity nor involve the iliac arteries.

The profile for delivery of a bifurcated stent graft is determined by the size of the main portion and each tubular portion of the bifurcated stent graft, as well as the configuration of the tubular portions in the delivery catheter such as branch portions placed side by side. It would be advantageous, if all the benefits of a bifurcated stent graft could be achieved with a lower delivery profile. A lower delivery profile would provide for a smaller sized delivery catheter, a smaller puncture size into the vasculature, and less trauma to the vascular tissue in passage of the delivery catheter through the vasculature. In addition, smaller catheters are more flexible, and the device may be able to be placed in more difficult to reach anatomical sites such as through smaller diameter vessels or through more tortuous pathways.

Therefore, there is a need for a medical device that is capable of effectively treating various target sites within the body such as an AAA. Moreover, there is a need for a medical device that may be easily delivered and adequately anchored at a target site such as within the aorta and common iliac arteries. In addition, there is a need for a medical device that may be delivered to a target site that is less traumatic to the vasculature and that may be used to prophylactically treat various conditions that may be more difficult to reach in the anatomy.

BRIEF SUMMARY OF THE INVENTION

Embodiments of the present invention may provide improvements over the prior art by, among other things, providing medical devices and methods for treating a target site within the body. For example, one embodiment provides a stent graft for treating a target site proximate to a bifurcated lumen, wherein the stent graft includes a first tubular structure having proximal and distal ends and a side wall extending therebetween. The first tubular structure includes an opening defined within the side wall and is configured to define a first portion having first and second ends and a second portion having first and second ends. The opening corresponds to the first ends of the first and second portions, and the second ends of the first and second portions respectively correspond to the proximal and distal ends of the first tubular structure and at least a portion of the first and second portions are configured to be positioned within respective branches of a bifurcated lumen. The first tubular structure comprises an expanded preset configuration and is configured to be constrained to a smaller diameter than the expanded preset configuration and return to the expanded preset configuration when unconstrained.

According to various aspects of the stent graft, the first tubular structure comprises at least one layer of an occlusive material or at least one layer of braided strands (e.g., strands of an elastic metallic alloy). The first tubular structure may include a bulbous region between its proximal and distal ends, and the opening may be defined in the bulbous region. The first ends of the first and second tubular portions may include at least one radiopaque marker and/or at least one hook configured to engage the lumen. In addition, at least a portion of an outer surface of the first and second portions may include a corrugated surface.

Additional variations of the stent graft include an opening defined by displacing the braided strands within the side wall of the first tubular structure. The opening may include a cut extending partially about the circumference of the first tubular structure such that the first tubular structure may be configured to be folded along the cut to form the first and second portions. The opening may be defined approximately midway between the proximal and distal ends of the first tubular structure. Moreover, the first tubular structure may be configured to be shaped along the opening such that the first and second portions comprise respective lumens extending between the first and second ends of the first and second portions that are not in fluid communication with one another. The first ends of the first and second portions may be D-shaped in cross section such that the first ends of the first and second portions are configured to cooperate to define a substantially circular opening.

According to one embodiment, the first ends of the first and second portions are configured to engage a lumen upstream of an aneurysm such that the opening substantially conforms to a diameter of the lumen. The second ends of the first and second portions may be configured to engage respective branches of the bifurcated lumen downstream of the aneurysm. The first and second portions may also be configured to be coaxially aligned for delivery within a catheter to reduce the delivery profile, to reduce trauma to the vessel, and improve the ease of delivery through smaller vessels and more difficult to reach anatomy.

An additional aspect of the stent graft further includes a second tubular structure having proximal and distal ends and a lumen extending therebetween that is configured to engage the first tubular structure, wherein the distal end of the second tubular structure comprises a pair of openings configured to receive the first tubular structure and align the lumen of the second tubular structure with the opening defined in the first tubular structure. The second tubular structure may include an expanded preset configuration, wherein the second tubular structure is configured to be constrained to a smaller diameter than the expanded preset configuration and return to the expanded preset configuration when unconstrained. The second tubular structure may further include a clamp configured to clamp the proximal end thereof so as to define the pair of openings. Furthermore, the first and second tubular portions may be configured to be delivered to the bifurcated lumen in axial alignment with one another.

An additional embodiment of the present invention includes a method for treating a target site proximate to a bifurcated lumen. The method includes constraining a first tubular structure to a smaller diameter than an expanded preset configuration (e.g., via axial elongation), wherein the first tubular structure has a proximal end and a distal end and an opening defined within a sidewall of the first tubular structure, and delivering the first tubular structure to the bifurcated lumen. The method further includes deploying the first tubular structure within the bifurcated lumen such that the first tubular structure self expands from the constrained smaller diameter, wherein deploying comprises shaping the first tubular structure proximate to the opening such that at least a portion of the first and second portions of the first tubular structure extend within respective branches of the bifurcated lumen and such that the opening is configured to direct fluid into each of the first and second portions.

Variations of the method include deploying the first tubular structure such that the first tubular structure engages the bifurcated lumen upstream and downstream of an aneurysm. The deploying step may include deploying the first tubular structure such that first ends of the first and second portions engage the bifurcated lumen upstream of an aneurysm and such that the opening substantially conforms to a diameter of the bifurcated lumen. The deploying step may also include deploying the first tubular structure such that second ends of the first and second portions that respectively correspond to the proximal and distal ends of the first tubular structure are configured to engage respective branches of the bifurcated lumen downstream of the aneurysm. In addition, the deploying step may include folding the first and second portions along the opening defined approximately midway between the proximal and distal ends of the first tubular structure. The deploying step may include engaging a distal end of the first or second portion, wherein shaping comprises inverting the first and second portions with respect to one another while engaging the distal end of the first or second portion. Moreover, the delivering step may include delivering the first tubular structure over at least one guide wire and/or delivering the first and second portions in coaxial alignment with one another.

An additional aspect of the method includes deploying a second tubular structure proximate to the first tubular structure such that a pair of openings defined in the second tubular structure are configured to receive the first tubular structure and align the lumen of the second tubular structure with the opening defined in the first tubular structure. Deploying the second tubular structure may include deploying a distal end of the second tubular structure in a lumen upstream of an aneurysm and a proximal end of the second tubular structure in the lumen downstream of the aneurysm.

An additional embodiment provides a method for fabricating a stent graft. The method includes braiding a first tubular structure about a mandrel, wherein the first tubular structure has a proximal end and a distal end and a sidewall extending therebetween. The method also includes shaping the first tubular structure so as to form first and second portions each having first and second ends, wherein at least a portion of the first and second portions may be configured to extend within respective branches of a bifurcated lumen. The method further includes defining an opening within the sidewall, wherein the opening is configured to correspond to the first ends of the first and second portions, and heat setting the first tubular structure while the first tubular structure is shaped.

Aspects of the method include braiding the first tubular structure into at least one layer with a plurality of strands. The shaping step may include folding the first tubular structure along the opening. For instance, the shaping step may include shaping the first tubular structure along the opening such that the first and second portions comprise respective lumens extending between the proximal and distal ends of the first and second portions that are not in fluid communication with one another. The defining step may include forming a cut partially about the circumference of the first tubular structure, wherein shaping comprises folding the first tubular structure along the cut. Alternatively, the defining step may include displacing braided strands of the first tubular structure to define the opening. In addition, the heat setting step may include heat setting the first tubular structure about a pair of D-shaped pins to define the opening.

According to an additional aspect, the method further includes braiding a second tubular structure on a mandrel, wherein the second tubular structure includes a proximal end and a distal end and a lumen extending therebetween. The method may further include defining a pair of openings in the second tubular structure that may be configured to receive the first tubular structure and align the lumen of the second tubular structure with the opening defined in the first tubular structure. Defining the pair of openings may include clamping the proximal end of the second tubular structure to define the pair of openings.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as a stent graft for excluding various vascular abnormalities, which may include, for example, excluding an aneurysm. The device may also be used as a flow restrictor or a shunt, filter or other type of device for placement in the vascular system, as well as a graft for lining a lumen of a vessel. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, or the like.

As explained in further detail below, a medical device according to one embodiment of the present invention is configured to treat a target site proximate to a bifurcated lumen. The medical device generally includes a tubular member that includes an opening in its sidewall and first and second portions configured to be positioned within respective branches of the bifurcated lumen. According to one embodiment, the medical device is a stent graft configured to treat an aneurysm located upstream of the branches of the bifurcated lumen. Moreover, the medical device may be delivered with the first and second portions in axial alignment with one another and then deployed within respective branches of the bifurcated lumen such that the medical device may be delivered in a small profile and exhibit flexibility for delivery within various contoured lumens.

According to one embodiment of the present invention for forming a medical device of the invention, the device includes a braided fabric formed of a plurality of wire strands having a predetermined relative orientation with respect to one another. Moreover, the device may comprise one or more layers of braided fabric or occlusive material such that the device may be a variety of occluding materials capable of at least partially inhibiting blood flow therethrough in order to facilitate the formation of thrombus and epithelialization around the device. Each layer may be a metallic material, a polymeric material, or a combination of such materials.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the target site could be assessed using various ultrasound echo doppler modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials and combinations of materials other than Nitinol that have elastic properties, such as spring stainless steel, alloys such as Elgiloy®, Hastelloy®, CoCrNi alloys (e.g., trade name Phynox), MP35N®, CoCrMo alloys, or polymeric materials. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One may solder, braze, weld, coat, glue, clamp, tie or otherwise affix the ends of the desired length together. According to one embodiment, each layer of the device may comprise 36-144 wire strands ranging in diameter from about 0.0005 to 0.010 in. and preferably about 0.001 to 0.006 in. formed of a shape memory alloy, such as Nitinol, that are braided so as to define fenestrations with an area of about 0.00015 to 0.015 sq. in., which are sufficiently small so as to slow the blood flow through the wall of the device and to facilitate thrombus formation thereon but sufficiently large enough to allow tissue in growth. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its heat-set shape in a deformed state. As explained in further detail below in conjunction with the illustrated embodiments, different configurations of devices may be formed and heat set for various locations within the body.

Those skilled in the art will appreciate that in order to speed up the occlusion of the vessel, the device may be coated with a suitable thrombogenic agent, filled with a polyester fiber, or braided with an increased number of wire strands. The interwoven fiber may attach to a clot to retain the clot firmly within the device as it forms the occlusion.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent an aneurysm for example.

The medical device can be constrained into its reduced diameter configuration and inserted into the lumen of the catheter. For instance, the medical device may be reduced to an outer diameter capable of being delivered within a catheter having an inner diameter of about 11 French or less, which is substantially smaller than conventional stent grafts for treatment of AAA. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g., by manually grasping the ends of the device and pulling them apart, which will tend to collapse the expanded diameter portions of the device inwardly toward the device's axis. In this regard, these devices are not unlike "Chinese handcuffs", which tend to constrict in diameter under axial tension. This stretched condition may provide a very low deliverable profile while maintaining excellent flexibility for ease of passage through smaller vessels and may allow for treatment of patients that may be otherwise difficult to treat due to build up of plaque caused by vascular disease which narrows the vessels leading to the treatment site.

If the device is to be used to permanently exclude a channel in the patient's body, one can simply retract the catheter and remove it from the patient's body. This will leave the medical device deployed in the patient's vascular system so that it may exclude the target site, such as an aneurysm or other channel in the patient's body. In some circumstances, the medical device may be attached to a delivery system in such a manner as to secure the device to the end of the delivery device. Before removing the catheter in such a system, it may be necessary to detach the medical device from the delivery device before removing the catheter and the delivery device. By keeping the medical device attached to the delivery device, the operator can retract the device for repositioning relative to the abnormal opening, if it is determined that the device is not properly positioned. A delivery device attached to the medical device may allow the operator to control the manner in which the medical device is deployed out the distal end of the catheter.

Although the device will tend to resiliently return to its initial expanded configuration, i.e., its shape prior to being collapsed for passage through the catheter, it should be understood that it might not always return entirely to that shape and that some manipulation of the device may be needed to assist in deployment. For example, it may be desirable that the device has a maximum outer diameter in its expanded configuration at least as large as and preferably larger than, the inner diameter of the opening in which it is to be deployed. For instance, the outer diameter of the device may be about 10-30% larger than the inner diameter of the opening. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat and retain the device therein.

When the device is deployed in a patient, thrombi will tend to collect on the surface of the strands. By having a greater strand density and smaller flow passages between strands as afforded by the multiple layer construction of the present invention, the total surface area of the strands and flow resistance will be increased, increasing the thrombotic activity of the device and permitting it to relatively rapidly occlude the wall of the stent graft and the aneurysm opening to exclude an aneurysm, but not occlude the vessel.

The device may be delivered and properly placed using two dimensional MRI, and/or Doppler color flow mapping. With the advent of these imaging technologies, the approximate anatomy of the defect can be visualized. The device that is employed will be based on the approximate size of the vessel or abnormality in which the device is to be placed.

The delivery catheter/sheath employed may take any suitable shape, such as an elongate flexible metal braided polymer tube configured to constrain the medical device and reach the target site. The delivery device may be an elongate flexible wire shaft or tube and may be used to urge the medical device through the lumen of a catheter/sheath for deployment in a channel of a patient's body. The delivery device may be connected to the proximal end of the device to retain positional control over the device. When the medical device is deployed out the distal end of the catheter, the delivery device may still retain it. The delivery device may be configured to release the device after proper placement is assured. As also explained in further detail below, the specific delivery method will depend on the particular device to be deployed within the body. For an exemplary discussion regarding delivery devices that may be employed, see U.S. Patent Appl. Publ. No. 2007/0118207 to Amplatz et. al., which is hereby incorporated in its entirety by reference.

Figure 1:
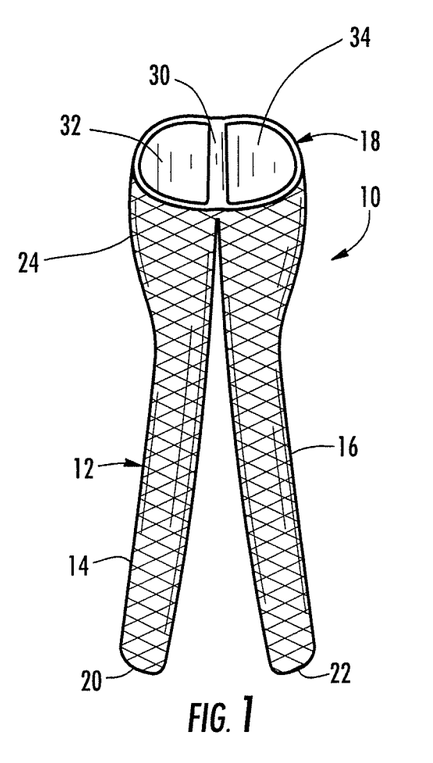
FIG. 1 illustrates a perspective view of a stent graft according to one embodiment of the present invention.

Referring now to the drawings, a discussion of the embodiments of various medical devices of the present invention will next be presented. FIG. 1 illustrates a first embodiment of a medical device 10 for treating a target site. For example, the medical device 10 could be a stent graft used for treating various body lumens, such as for treating an aneurysm. The medical device 10 includes a tubular structure 12 configured to be shaped into a pair of tubular portions 14, 16 for positioning within respective branches of a bifurcated lumen. An opening 18 is defined in the sidewall of the tubular structure 12 which facilitates fluid flow through the tubular portions 14, 16 in order to treat a target site as explained in further detail below.

Figure 2:
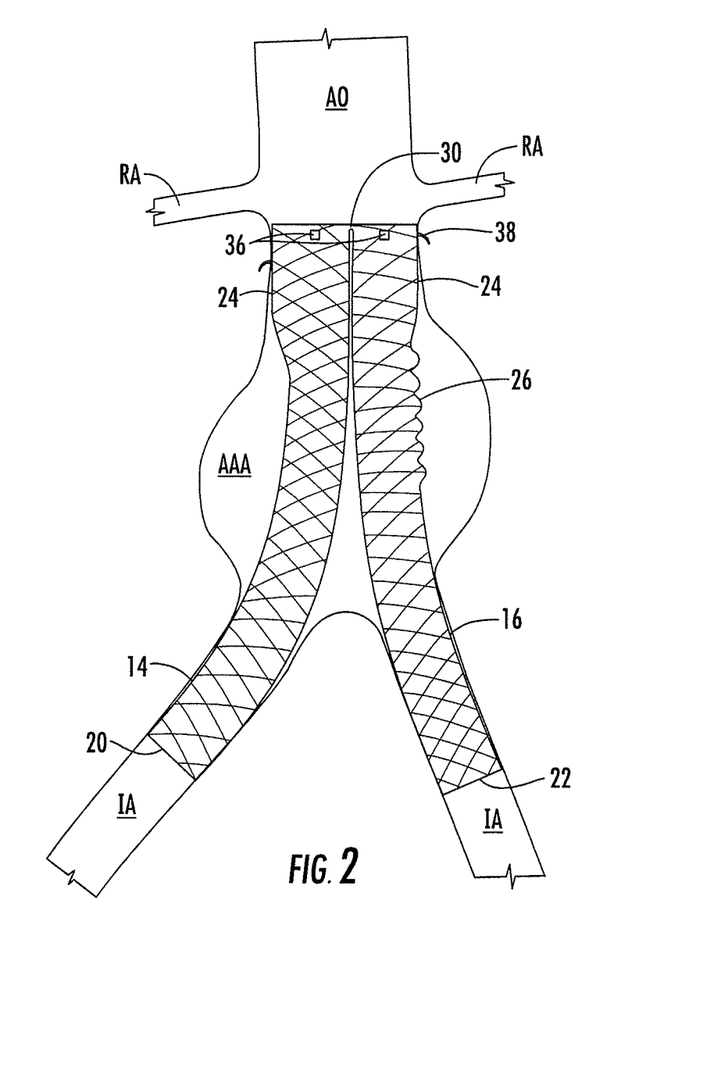
FIG. 2 depicts a side elevational view of a stent graft positioned within a bifurcated lumen for treating an aneurysm according to one embodiment of the present invention.
Figure 3:
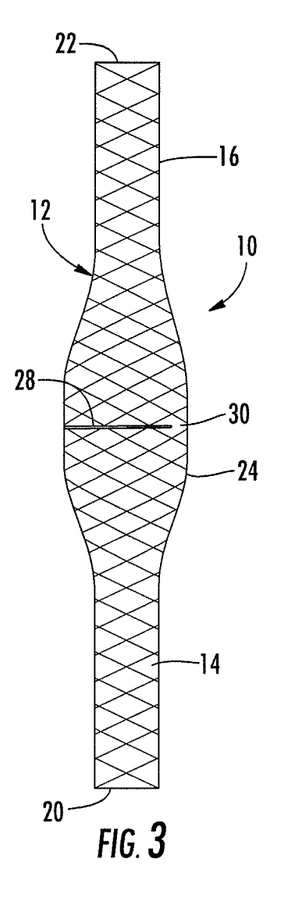
FIG. 3 illustrates a side elevational view of a stent graft having a pair of tubular members coaxially aligned according to an embodiment of the present invention.

As shown in FIG. 3, the tubular structure 12 includes proximal 20 and distal 22 ends and a lumen or longitudinal passageway extending therebetween. The tubular structure 12 may be cylindrical and have a constant diameter along its length or be other shapes and sizes. For example, the tubular structure 12 may include a bulbous portion 24 positioned between its proximal 20 and distal 22 ends. Furthermore, the tubular structure 12 may include a generally smooth surface or one or more corrugated portions 26 as shown in FIG. 2. As indicated above, the tubular structure 12 may comprise one or more layers of braided fabric and heat set into a preset memorized configuration.

An opening 18 is defined in the sidewall of the tubular structure 12. For example, the opening 18 may be defined in the tubular structure 12 by forming a cut 28 through the sidewall of the tubular structure. The cut 28 may be formed partially about the circumference of the tubular structure 12 to define a hinge 30 such that the tubular structure may be shaped about the hinge. For instance, the cut 28 may be formed about ¾ of the circumference of the tubular structure 12. Thus, the tubular structure 12 may be folded about the hinge 30 (e.g., about 180°) to define the tubular portions 14, 16 as shown in FIGS. 1 and 2. The opening 18 could be formed approximately midway between the proximal 20 and distal 22 ends of the tubular structure or could be formed at any other desired location whereby the tubular portions 14, 16 may be formed.

Figure 2A:
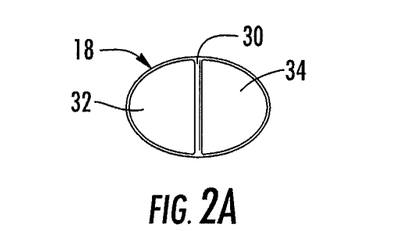
FIG. 2A depicts an end view of the stent graft shown in FIG. 2.

As shown in FIG. 2A, each tubular portion 14, 16 may have a D-shaped cross section such that the tubular portions cooperate to define a circular cross section. Thus, the tubular portions 14, 16 may be configured to engage and seal a lumen such as the descending aorta ("AO") as shown in FIG. 2. Moreover, FIG. 2A illustrates that the opening 18 is defined such that each tubular member 14, 16 has a respective lumen 32, 34 extending therethrough that is not in fluid communication with one another. As such, FIG. 2 shows that each tubular portion 14, 16 may be configured to extend from a lumen (e.g., AO) upstream of a target site such as an aneurysm ("AAA") and into respective branches of a bifurcated lumen such as the common iliac arteries ("IA"). As such, the proximal 20 and distal 22 ends of the tubular structure 12 are configured to be positioned in respective IA's when shaped about the hinge 30 and positioned within respective branches of the bifurcated lumen. Moreover, the opening 18 is capable of being positioned just below the renal arteries ("RA") to avoid blocking the flow of blood out of the RA's. In order to facilitate positioning of the medical device 10, each tubular portion 14, 16 may include one or more radiopaque markers 36 (e.g., platinum or NiTi) proximate to the opening 18 or at any other location if desired. In addition, the tubular portions 14, 16 may include one or more hooks 38 for facilitating fixation within the lumen such as the AO.

Figure 4:
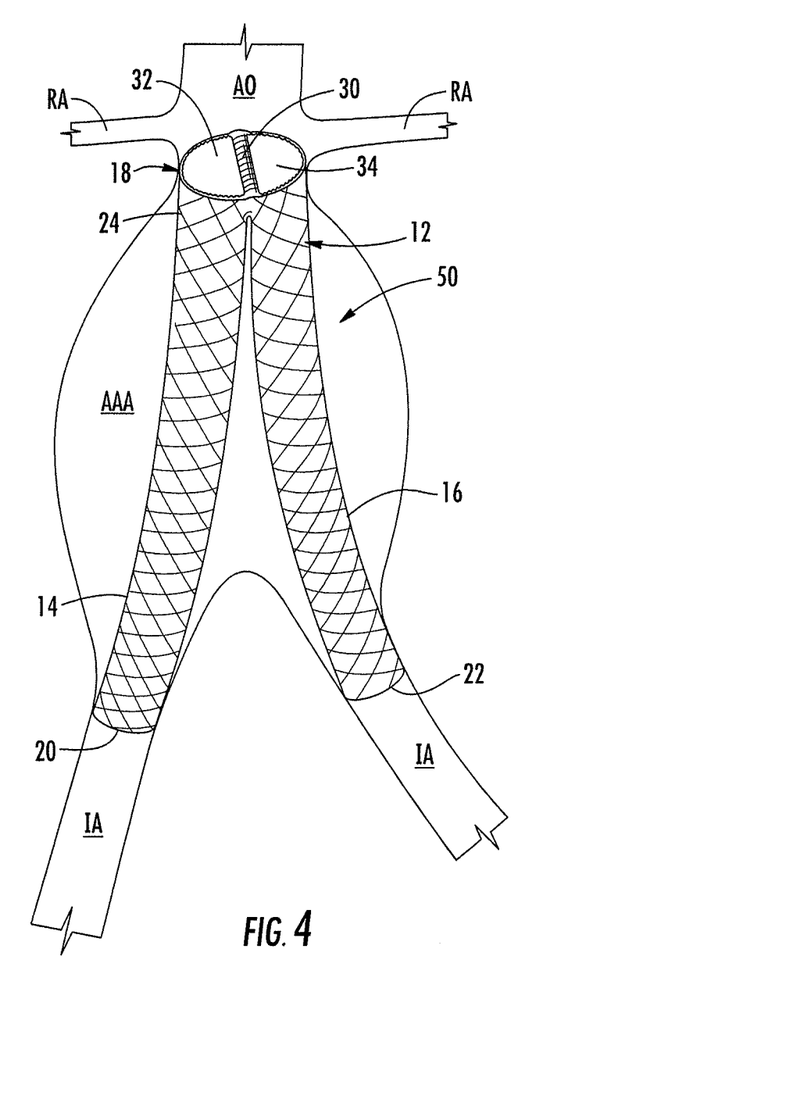
FIG. 4 shows a stent graft positioned within a bifurcated lumen for treating an aneurysm according to an additional embodiment of the present invention.

FIG. 4 illustrates a medical device 50 according to an additional embodiment of the present invention. The medical device 50 is similar to the medical device 10 discussed above but includes a substantially cylindrical tubular structure 12 along its length. In addition, the tubular structure 12 may include one or more layers of braided fabric, and the opening 18 may be formed by displacing the braided strands. In other words, the opening 18 may be formed by displacing adjacent braided strands away from one another define an opening. For example, a pair of D-shaped pins could be inserted within each of the tubular portions 14, 16, and the strands could be displaced around the D-shaped pins and heat set to define the opening 18. Moreover, the tubular structure 12 could be shaped by bending along the hinge 30 and forming respective lumens 32, 34 and heat setting the tubular structure in a desired configuration.

As indicated above, the medical devices 10, 50 may be formed from one or more layers of braided fabric and heat set into a desired configuration. For example, the tubular structure 12 may first be formed on a mandrel having a desired shape and then shaped into a desired final shape, as such as that shown in FIG. 1. Once the tubular structure 12 is in a desired shape, including the size and shape of the opening 18, the tubular structure is heat set at a particular temperature and for a particular time as known to those of ordinary skill in the art. The heat set temperature induces a phase change which causes the material to have a configuration that can be fixed by heating the material above a certain transition temperature to induce a change in the phase of the material. When the material is cooled back down, the material will "remember" the shape it was in during the heat treatment and will tend to assume that configuration unless constrained from so doing. After heat setting, the tubular structure 12 may be constrained for delivery within a delivery device, such as by axial elongation, and self expand and return to its expanded preset configuration when deployed from the delivery device. Thus, the tubular structure 12 is resilient and has the tendency to return to its preset, memorized configuration after any external forces are removed.

Figure 5:
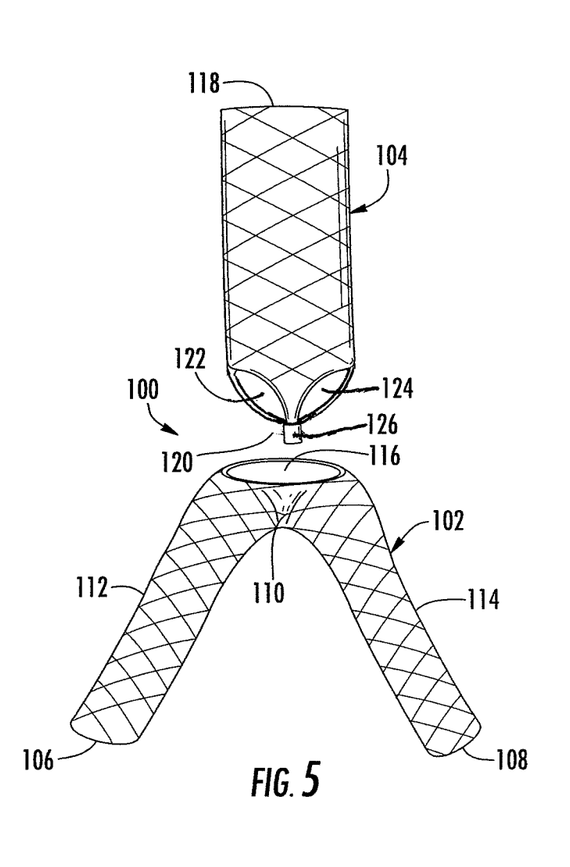
FIG. 5 illustrates a stent graft according to one embodiment of the present invention.
Figure 6:
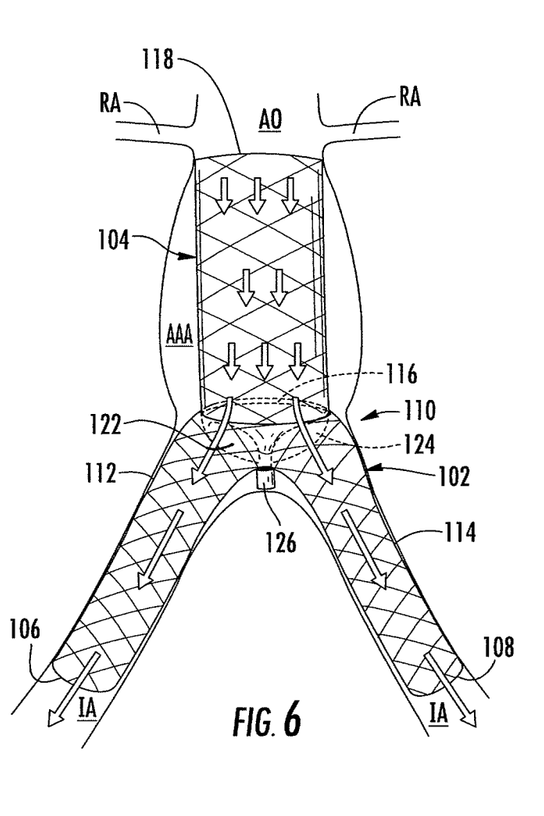
FIG. 6 depicts the stent graft of FIG. 5 positioned within a bifurcated lumen for treating an aneurysm according to an embodiment of the present invention.

FIGS. 5 and 6 illustrate a medical device 100 according to another embodiment of the present invention. In this particular embodiment, the medical device 100 generally includes a first tubular structure 102 and a second tubular structure 104 configured to engage one another. The first 102 and second 104 tubular structures could be generally cylindrical in shape or be various other shapes such as by including one or more bulbous regions or corrugated surfaces. Moreover, the 102 and second 104 tubular structures may be one or more layers of braided fabric material as described above.

The first tubular structure 102 has proximal 106 and distal 108 ends and is configured to be shaped along hinge 110 to define first 112 and second 114 tubular portions. Similar to the embodiments described above, the tubular structure 102 includes an opening 116 defined in its sidewall between its proximal 106 and distal 108 ends. The opening 116 could be formed using various techniques such as by displacing strands of braided fabric in the sidewall or cutting through the sidewall and then heat setting the tubular structure 102. As shown in FIG. 6, the first tubular structure 102 is configured to be positioned within respective branches of a bifurcated lumen, such as the IA's.

The second tubular structure 104 has proximal 118 and distal 120 ends and a pair of openings 122, 124 defined at its distal end. The openings 122, 124 could be formed, for instance, by displacement of wires about two pins placed in the side wall and by clamping the strand ends at distal end 120 with a clamp 126 and heat setting the tubular structure 104. FIG. 6 shows that the second tubular structure 104 is capable of being positioned within a lumen, such as within the AO, and spanning a target site, such as an aneurysm located between the RA's and IA's.

FIG. 6 further illustrates that the openings 122, 124 are configured to receive the first tubular structure 102 and align with the opening 116 defined in the first tubular structure. In particular, the distal end 108 of the first tubular structure 102 is capable of being delivered through a first branch of a bifurcated lumen, through the first opening 122, through the second opening 124, and then into the second branch of a bifurcated lumen. The diameters of the openings 122, 124 are slightly smaller than the diameter of the first tubular structure 102, such that the self expansion of the first tubular structure causes an abutment against the openings 122, 124. The diameter of the opening 116 is sized and configured to align with the openings 122, 124 and the main lumen of the second tubular structure such as not to restrict flow into the tubular portions 112, 114. As shown in FIG. 6, blood flowing through the AO is capable of flowing through the second tubular structure 104, into opening 116, and into respective tubular portions 112, 114 positioned in the IA's. As indicated above, the medical device 100 may be formed from a braided fabric and heat set in a desired configuration. For example, the first 102 and second 104 tubular structures may be separately formed on respective mandrels and heat set. After heat setting, the first 102 and second 104 tubular structures may be constrained for delivery within a delivery device, such as by axial elongation, and resiliently self expand and return to their expanded preset configuration when deployed from the delivery device.

Figure 7A:
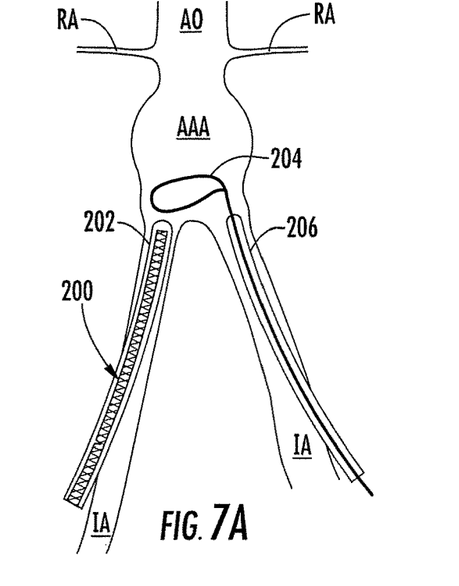
FIGS. 7A-7H illustrate a delivery method for delivering a stent graft according to one embodiment of the present invention.
Figure 7B:
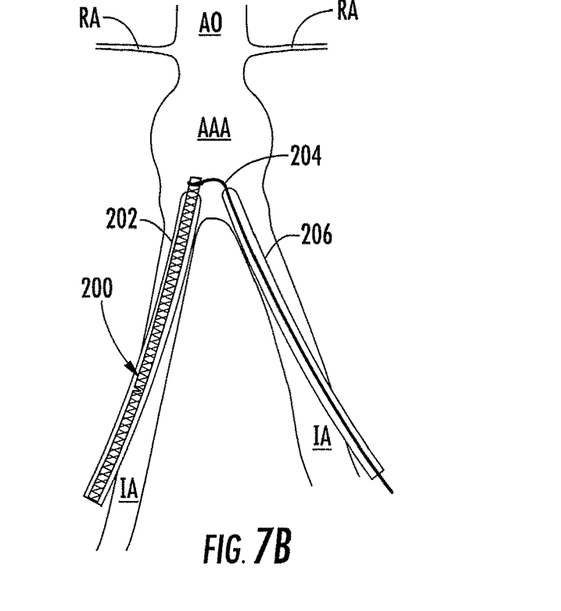
Figure 7C:
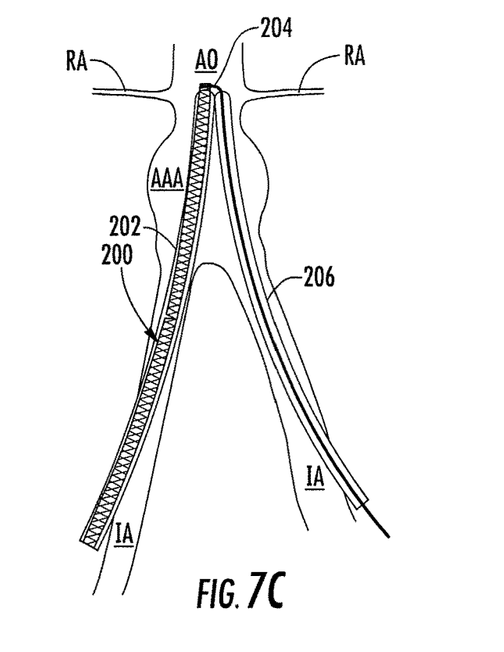
Figure 9:
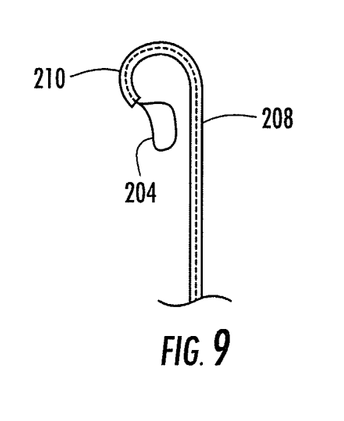
FIG. 9 depicts a partial view of a snare according to one embodiment of the present invention.

As described in general above, different delivery techniques may be employed to deliver and deploy a medical device into a lumen for treating a target site. FIGS. 7A-7H illustrate one embodiment of delivering a medical device for treating an AAA, wherein such method could be used to deliver the medical devices illustrated in FIGS. 1-4. In this regard, FIG. 7A shows a medical device 200 positioned within a delivery catheter 202 is first delivered through the right IA, while a snare 204 positioned within a catheter 206 is delivered through the left IA. The snare 204 and catheter 206 could be any conventional device known to those of ordinary skill in the art. Alternatively, the snare 204 could be delivered through a tube 208 having a curved portion 210 at its distal end as shown in FIG. 9. The curved portion 210 could be heat set into a desired curvature. The curved portion 110 may facilitate delivery of the medical device 200 by flipping the distal end of the medical device and orienting the end in the direction of flow during deployment.

Figure 7D:
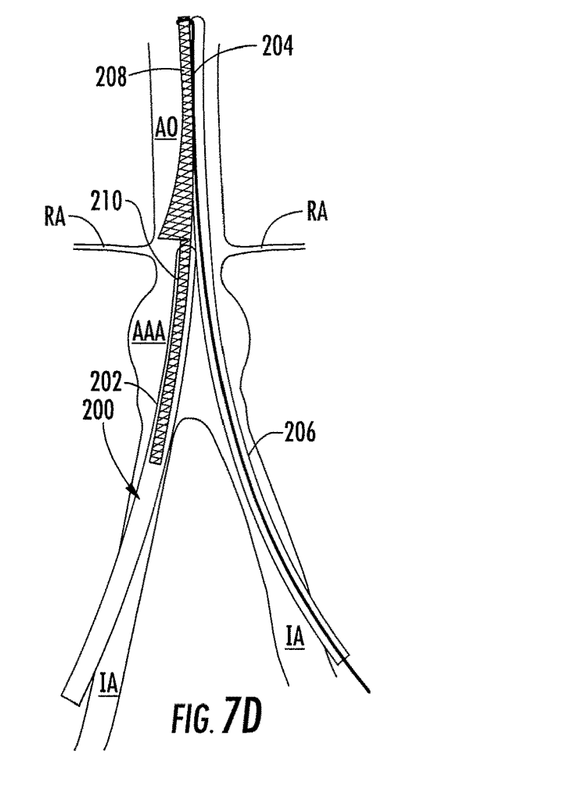
Figure 7E:
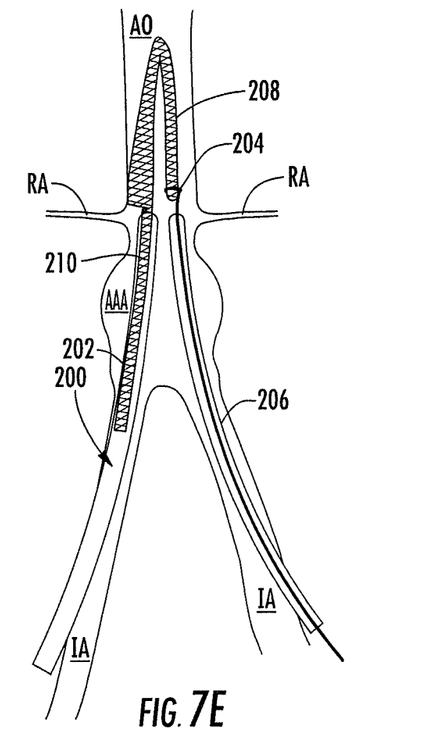
Figure 7F:
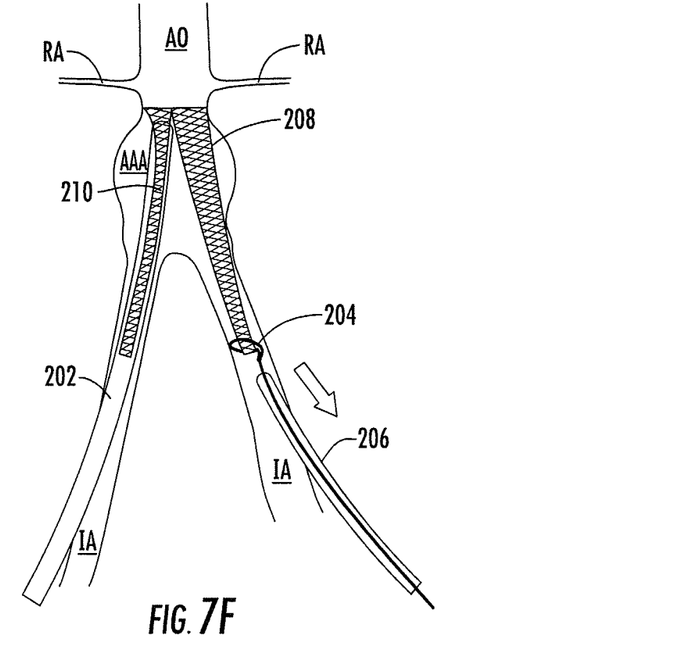
Figure 7G:
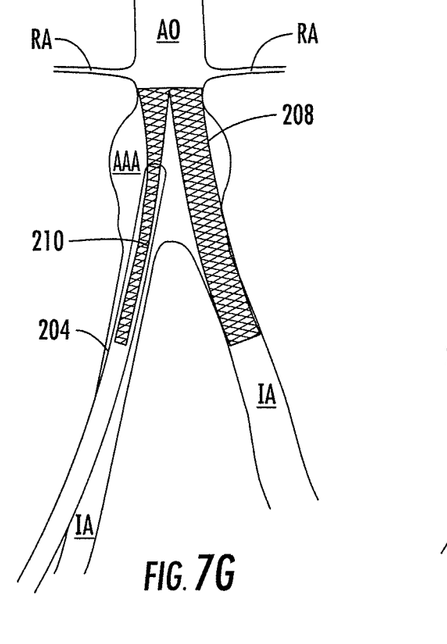
Figure 7H:
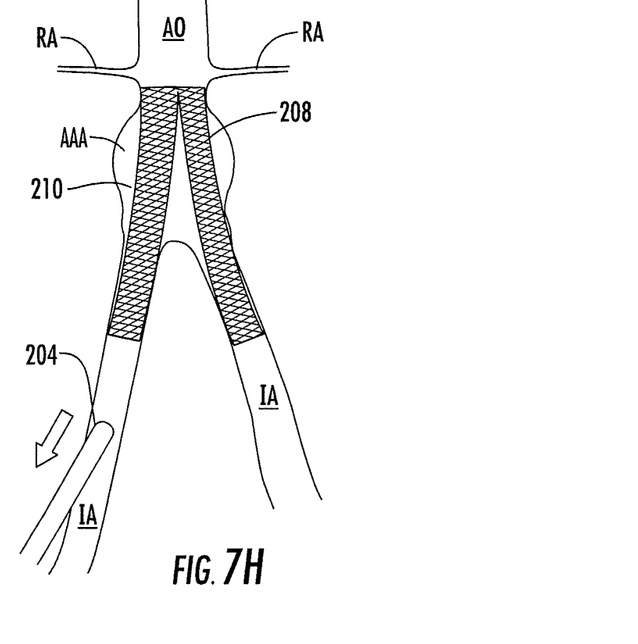

Referring again to FIGS. 7A-7H, the distal end of the medical device 200 is partially deployed from the delivery catheter 202 so that the snare 204 may engage a portion of the device near the distal end as shown in FIG. 7B, and the distal end of the medical device is advanced proximate to the RA's while engaged with the snare 204 as shown in FIG. 7C. While holding the delivery catheter 202 stationary, the snare 204 is moved upstream of the RA's in order to deploy a first tubular portion 208 (FIG. 7D). To facilitate this movement the graft delivery device may be advanced distal to move the graft distally through the delivery catheter 202. The first tubular portion 208 may self-expand when released from the delivery catheter unless the snare maintains axial tension on the tubular portion. The snare 204 may then be retracted downstream in order to invert the first tubular portion 208 as depicted in FIG. 7E. FIG. 7F demonstrates that further retraction of the snare 204 back into the left IA results in full inversion of the first tubular portion 208 except for the end portion held by the snare 204. Full deployment of tubular portion 208 may be accomplished by relaxing tension on the snare 204 to allow the end of the tubular portion 208 near the RA to self expand against the aortic wall. By lightly releasing the snare grasp on the distal end portion and pulling the snare proximally out of the body, the distal end portion of the device may be inverted and the tubular portion 208 may self expand. The tubular portion 210 may now be deployed by retracting the delivery catheter 202 proximally out of the left IA while advancing the delivery device in order to deploy the second tubular portion 210 as shown in FIGS. 7G and 7H. Once the tubular segment 210 is positioned as desired the delivery device may be released from the graft 200 and the delivery device and delivery catheter 202 may be removed from the body. Thus, when deployed the first 208 and second 210 tubular portions may engage and seal the AO downstream of the RA's, bridge an AAA, and engage and seal the left and right IA's. Although not shown, it is understood that an introducer catheter may be placed in each of the right and left femoral artery that leads to the IA's to facilitate vascular access to each artery, as well delivery of the delivery catheters or other instruments.

Figure 8A:
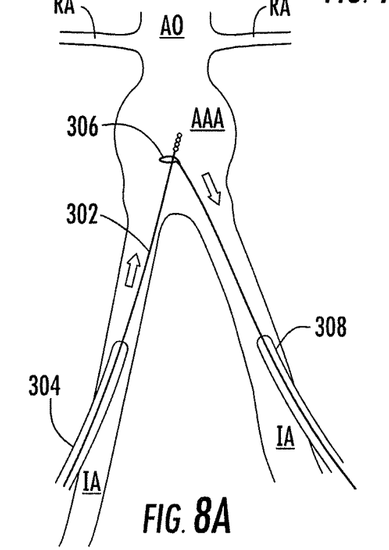
FIGS. 8A-8G depict a delivery method for delivering a stent graft according to an additional embodiment of the present invention.
Figure 8B:
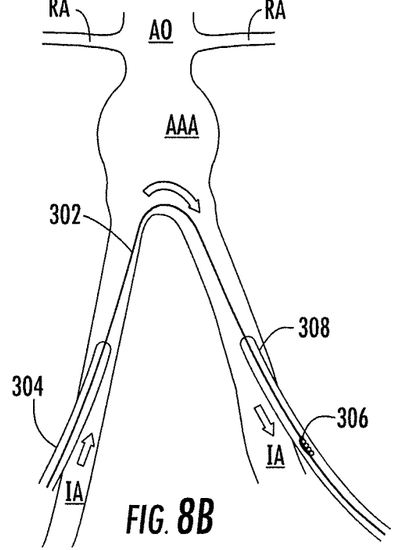
Figure 8C:
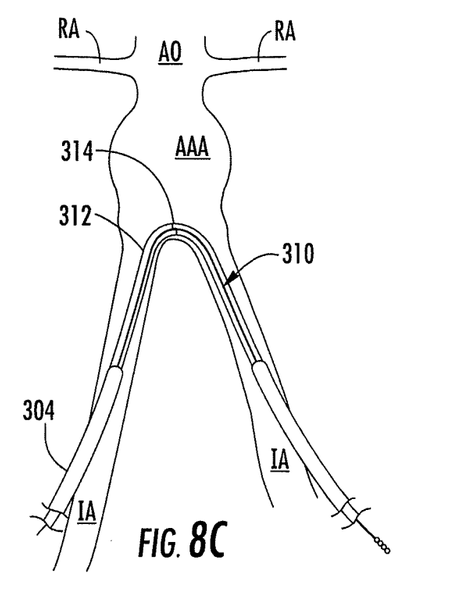
Figure 10:
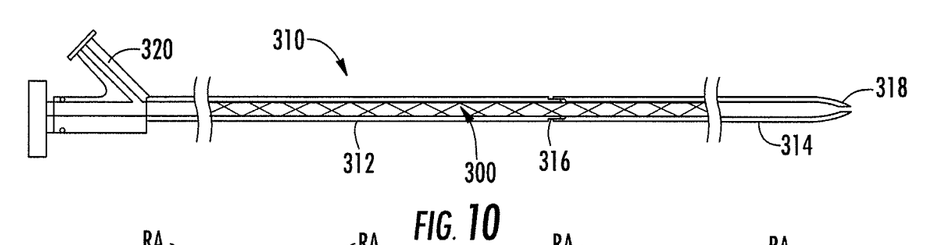
FIG. 10 illustrates a delivery device according to one embodiment of the present invention.

FIGS. 8A-8G illustrate an additional embodiment for delivering and deploying a medical device 300, which could alternatively be used to deploy the medical devices 10, 50 discussed above in conjunction with FIGS. 1-4. FIG. 8A shows that a first guide wire 302 is advanced though a first introducer 304 and into the right IA, while a snare 306 is advanced through a second introducer 308 in order to engage the end of the first guide wire. While engaged with the first guide wire 302, the snare 306 may be retracted to pull the first guide wire into and through the second introducer 308 as shown in FIG. 8B. A two-part delivery device 310 having a medical device 300 disposed therein may then be inserted over the first guide wire 302 though the first introducer 304 and into and through the second introducer 308 (FIG. 8C). FIG. 10 illustrates in further detail that the delivery device 310 may include a proximal sheath 312 and a distal sheath 314. The delivery device 310 may also include a releasable joint 316 that facilitates separation of the proximal 312 and distal 314 sheaths. Thus, pulling the proximal 312 and distal 314 sheaths away from one another facilitates separation of the sheaths at the releasable joint. The delivery device 310 could include other features such as a distal taper 318 for facilitating insertion within the sheaths 312, 314 and Y-adapter 320 for receiving and guiding a guide wire through the sheaths.

Figure 8D:
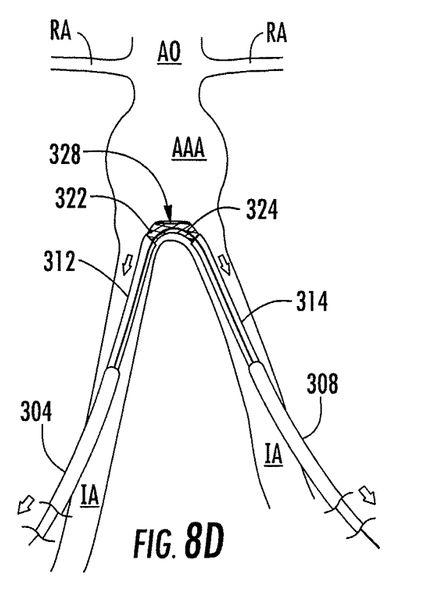
Figure 8E:
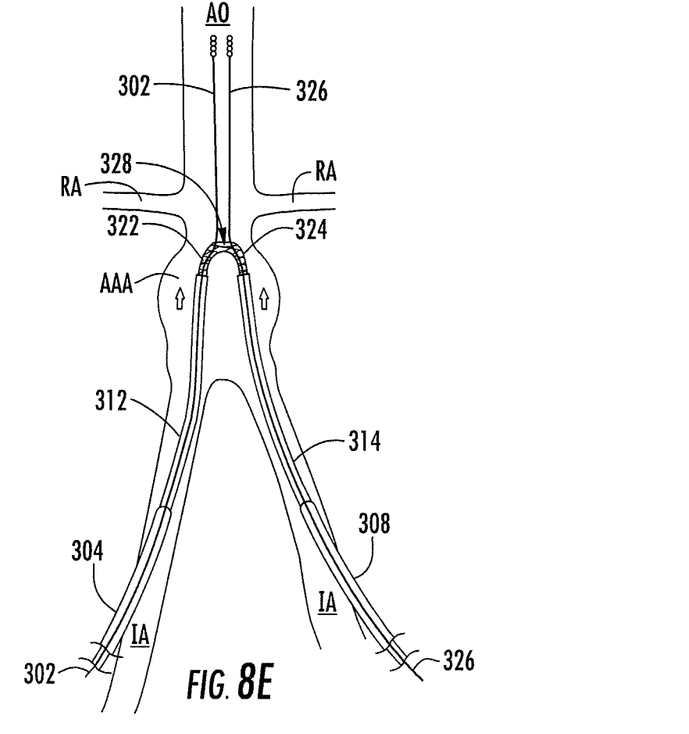
Figure 8F:
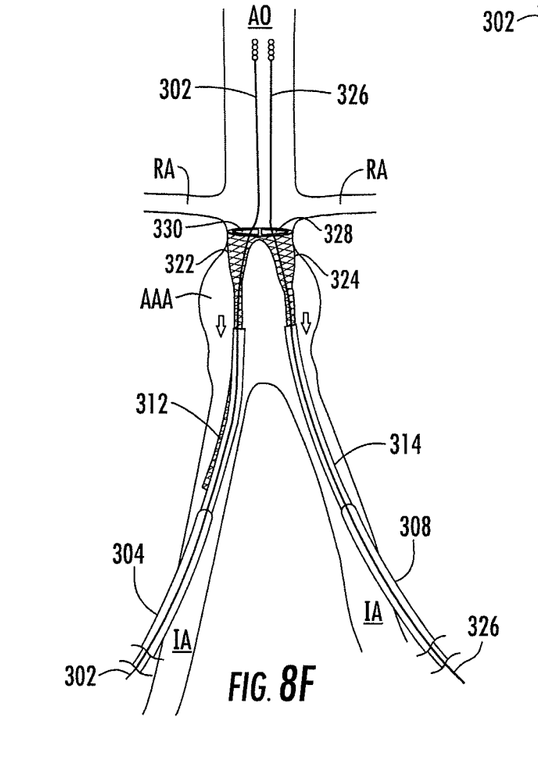
Figure 8G:
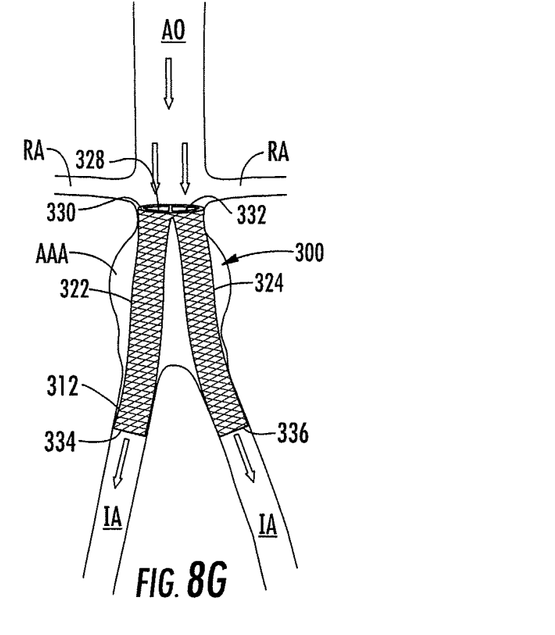

The medical device 300 may be positioned within the delivery device 310 such that the releasable joint aligns approximately with the midpoint of the medical device, such as proximate to the hinge between the tubular portions 322, 324. Furthermore, the medical device 300 may be delivered such that the tubular portions 322, 324 are in axial alignment with one another as shown in FIG. 10. Once the delivery device 310 is positioned within the first 304 and second 308 introducers with the releasable joint 316 located upstream of the IA's as shown in FIG. 8C, the proximal 312 and distal 314 sheaths may be partially withdrawn to partially expose an opening 328 defined in the medical device as shown in FIG. 8D. The first guide wire 302 may be first withdrawn proximally until the end of the guidewire is at the opening 328 and then may be advanced through the opening 328 and upstream of the RA's, while a second guide wire 326 may be inserted within the distal sheath 314, through the opening 328, and upstream of the RA's as shown in FIG. 8E. FIG. 8F shows in further detail that the opening 328 is defined such that each tubular portion 322, 324 includes a respective lumen 330, 332 extending therethrough that are not in fluid communication with one another. The opening 328 is positioned slightly downstream of the RA's and as the proximal 312 and distal 314 sheaths are further retracted out of the IA's the opening 328 expands against the AO wall to serve as an anchor. Further retraction of sheaths 312, 314 allows the tubular portions 322, 324 to self expand and also engage the AO (FIG. 8F). In order to fully deploy the medical device 300, the proximal 312 and distal 314 sheaths are completely retracted from respective IA's while the delivery device is used to maintain positional control over the tubular portion 322. After the device is confirmed to be in the desired location, the delivery device, the guide wires 302, 326 and introducers 304, 308 are removed from respective IA's (FIG. 8H). When completely deployed, the opening 328 and adjacent legs engage and seal the AO, while the tubular proximal portions 322, 324 engage and seal respective IA's. Therefore, blood flowing through the opening 328 enters respective lumens 330, 332 of respective tubular portions 322, 324 and out of the proximal 334 and distal 336 ends of the medical device 300, thereby diverting blood away from the AAA to reduce growth and/or pressure on the AAA.

The medical device 100 illustrated in FIGS. 5 and 6 may be delivered using a different technique than that of the medical devices 10, 50. For instance, the second tubular structure 104 may be constrained to a smaller diameter than its preset expanded configuration and delivered through the femoral artery, into the IA and into the AO using an introducer sheath, delivery catheter or sheath, a delivery device and, optionally, over a guide wire. The distal end of the delivery sheath would be positioned downstream of the RA's, and the delivery sheath may be retracted while holding the delivery device in place to expose the proximal end 118 of the second tubular structure 104. Further retraction of the delivery sheath and advancement of the delivery device would result in deployment and self expansion of the remaining portion of the medical device 100. Radiopaque markers may be placed on the device to aid in angular orientation such that the distal openings 122, 124 are properly aligned with the ostia of the IA's.

As shown in FIG. 6, the second tubular structure 104 would be positioned to span the AAA upstream of the IA's and downstream of the RA's. The first tubular structure 102 may then be delivered through one of the IA's to engage the second tubular structure 104. In particular, the first tubular structure 102 may be constrained to a smaller diameter than its preset expanded configuration and positioned within a delivery sheath and attached to a delivery device at the proximal end, and delivered into one of the IA's either with or without a guide wire. For example, the distal end of the delivery sheath may be advanced through the right IA, through the openings 122, 124 in the second tubular structure 104 and into the left IA until the opening 116 in the first tubular structure aligns with the openings in the second tubular structure. Radiopaque markers may be positioned on the device to aid in angular orientation and alignment of the openings. When in a desired position, the delivery sheath may be retracted while holding back and/or advancing the delivery device in order to deploy the first tubular structure 102. To facilitate the delivery over the iliac bifurcation arch is may be desirable that the delivery catheter/sheath be a steerable sheath or have a pre-shaped tip to cross the arch and lead from the first iliac artery through the openings 122, 124 and into the second iliac artery. Furthermore, the first 102 and second 104 tubular structures could be delivered within the same delivery sheath and disposed in axial alignment with one another or could be delivered in respective delivery sheaths.

Embodiments of the present invention may provide several advantages. For example, a medical device for treating a target site proximate to a bifurcated lumen is provided. The medical device may be a stent graft for treating an aneurysm that may effectively exclude the aneurysm. In addition, the stent graft may be configured to treat an AAA while ensuring adequate fixation without blocking the RA's or otherwise interfering with the flow of blood through the AO and into the IA's. Furthermore, the medical device is capable of being delivered as a tubular member within a delivery catheter using a variety of techniques. Thus, the medical device may be delivered within a catheter having a smaller inner diameter than medical devices that may not otherwise be capable of being delivered coaxially. Therefore, the medical device may provide the benefits of a stent graft for treating a target site proximate to a bifurcated lumen after deployment while providing the benefits of a single tubular stent graft prior to deployment. As such, the device may be capable of being delivered to harder to access locations within the body, as well as be delivered through smaller diameter vessels, openings, cavities, and the like. Moreover, the medical device may be used to occlude, shunt, restrict flow, or reline vessels, lumens, cavities, aneurysms, or organs anywhere in the vasculature or body.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for fabricating a stent graft comprising:
   braiding a first tubular structure about a mandrel, the first tubular structure having a proximal end, and a distal end, and a sidewall extending therebetween;
   shaping the first tubular structure so as to form first and second portions each having first and second ends, wherein at least a portion of the first and second portions are configured to extend within respective braches of a bifurcated lumen;
   defining an opening within the sidewall, wherein the opening is configured to correspond to the first ends of the first and second portions; and
   heat setting the first tubular structure.

2. The method of claim 1, wherein braiding comprises braiding a plurality of strands into at least one layer.

3. The method of claim 1, wherein the first tubular structure comprises a corrugated surface.

4. The method of claim 1, wherein shaping comprises folding the first tubular structure along the opening.

5. The method of claim 4, wherein folding comprises folding the first tubular structure along the opening to define a hinge.

6. The method of claim 1, wherein defining comprises forming a cut partially about the circumference of the first tubular structure, and wherein shaping comprises folding the first tubular structure along the cut.

7. The method of claim 1, wherein defining comprises forming a cut partially about a circumference of the first tubular structure and within a bulbous portion positioned between the proximal end and the distal end of the first tubular structure.

8. The method of claim 2, wherein defining comprises displacing braided strands of the first tubular structure to define the opening.

9. The method of claim 8, wherein displacing braided strands of the first tubular structure defines the opening approximately midway between the proximal end and the distal end of the first tubular structure.

10. The method of claim 1, wherein heat setting comprises heat setting the first tubular structure about a pair of D-shaped pins to define the opening.

11. The method of claim 1, wherein shaping comprises shaping the first tubular structure along the opening such that the first and second portions comprise respective lumens extending between proximal and distal ends of the first and second portions that are not in fluid communication with one another.

12. The method of claim 1, further comprising:
    coating the first tubular structure with a thrombogenic agent.

13. The method of claim 1, further comprising:
    filling the first tubular structure with a polyester fiber.

14. The method of claim 1, further comprising:
    attaching a radiopaque marker to at least one of the first end of the first portion and the first end of the second portion.

15. The method of claim 1, further comprising:
    attaching one or more hooks to the first tubular structure for facilitating fixation of the first tubular structure to the bifurcated lumen.

16. The method of claim 1, further comprising:
    braiding a second tubular structure on a mandrel, the second tubular structure comprising a proximal end and a distal end and lumen extending therebetween.

17. The method of claim 16, further comprising:
    defining a pair of openings in the second tubular structure configured to receive the first tubular structure and align the lumen of the second tubular structure with the opening defined in the first tubular structure.

18. The method of claim 17, wherein defining the pair of openings comprises clamping the proximal end of the second tubular structure to define the pair of openings.

* * * * *